(12) United States Patent
Lakkireddy et al.

(10) Patent No.: US 11,627,882 B2
(45) Date of Patent: Apr. 18, 2023

(54) ESOPHAGEAL MANAGEMENT SYSTEM FOR USE IN DISPLACING AN ESOPHAGUS DURING A MEDICAL PROCEDURE

(71) Applicant: Chelak Medical Solution Inc., Houston, TX (US)

(72) Inventors: Dhanunjaya Lakkireddy, Leawood, KS (US); Jie Cheng, Houston, TX (US)

(73) Assignee: CHELAK MEDICAL SOLUTION INC., Houston, TX (US)

( * ) Notice: Subject to any disclaimer, the term of this patent is extended or adjusted under 35 U.S.C. 154(b) by 584 days.

(21) Appl. No.: 16/253,778

(22) Filed: Jan. 22, 2019

(65) Prior Publication Data
US 2019/0223734 A1   Jul. 25, 2019

Related U.S. Application Data

(60) Provisional application No. 62/620,001, filed on Jan. 22, 2018.

(51) Int. Cl.
*A61B 5/01* (2006.01)
*G01K 11/3206* (2021.01)
(Continued)

(52) U.S. Cl.
CPC ............. *A61B 5/01* (2013.01); *A61B 5/6847* (2013.01); *A61B 6/481* (2013.01); *A61B 6/487* (2013.01);
(Continued)

(58) Field of Classification Search
CPC ......... A61B 5/01; A61B 5/6847; A61B 6/487; A61B 6/481; A61B 17/0218; A61B 18/00; A61B 90/39
See application file for complete search history.

(56) References Cited

U.S. PATENT DOCUMENTS 5,357,954 A * 10/1994 Shigezawa ........... A61B 5/4233
600/528
6,689,062 B1   2/2004 Mesallum
(Continued)

FOREIGN PATENT DOCUMENTS

WO   2010/102117 A1   9/2010
WO   2013/030749 A2   3/2013

OTHER PUBLICATIONS

Rahul Bhardwaj, MD, et al., "Esophageal Deviation during Atrial Fibrillation Ablation, JACC: Clinical Electrophysiology," The American College of Cardiology Foundation vol. 4, No. 8, 2018, pp. 1020-1030.
(Continued)

*Primary Examiner* — Joseph M Dietrich
(74) *Attorney, Agent, or Firm* — Cooley LLP

(57) ABSTRACT

Certain aspects of the present disclosure provide methods and apparatus for managing an esophagus of a subject during a medical procedure, such as cardiac tissue ablation or bronchial tissue ablation. Managing the esophagus may include displacing the esophagus, imaging the esophagus, and/or measuring temperature at one or more locations inside the esophagus. One example esophageal management system generally includes a tube configured for insertion through a mouth and into the esophagus of the subject. The tube generally includes a first port located at a proximal end of the tube and in fluid communication with a distal portion of the tube via a first path, a second port located at the proximal end of the tube, and a third port located between the proximal end of the tube and a distal end of the tube and in fluid communication with the second port via a second path.

14 Claims, 8 Drawing Sheets

(51) Int. Cl.
| | |
|---|---|
| *G01K 13/20* | (2021.01) |
| *A61B 90/00* | (2016.01) |
| *A61B 5/00* | (2006.01) |
| *A61B 6/00* | (2006.01) |
| *A61B 17/02* | (2006.01) |
| *A61B 18/00* | (2006.01) |
| *A61B 18/14* | (2006.01) |
| *A61B 17/00* | (2006.01) |

(52) U.S. Cl.
CPC .......... *A61B 17/0218* (2013.01); *A61B 18/00* (2013.01); *A61B 90/39* (2016.02); *G01K 11/3206* (2013.01); *G01K 13/20* (2021.01); *A61B 5/687* (2013.01); *A61B 18/1492* (2013.01); *A61B 2017/003* (2013.01); *A61B 2018/00351* (2013.01); *A61B 2018/00577* (2013.01); *A61B 2018/00642* (2013.01); *A61B 2018/00678* (2013.01); *A61B 2018/00708* (2013.01); *A61B 2018/00791* (2013.01); *A61B 2090/0427* (2016.02); *A61B 2090/0481* (2016.02); *A61B 2090/3966* (2016.02)

(56) References Cited

U.S. PATENT DOCUMENTS

| | | | |
|---|---|---|---|
| 7,153,299 | B1 | 12/2006 | Tu et al. |
| 2008/0097422 | A1* | 4/2008 | Edwards ............ A61B 18/1206 606/34 |
| 2009/0069875 | A1 | 3/2009 | Fishel |
| 2011/0034936 | A1 | 2/2011 | Maloney |
| 2014/0012155 | A1* | 1/2014 | Flaherty ................. A61B 5/015 600/549 |
| 2016/0262627 | A1* | 9/2016 | Hecker .................... A61B 5/08 |

OTHER PUBLICATIONS

Carola Gianni, MD, PhD, et al., "Difference in thermodynamics between two types of esophageal temperature probes: Insights from an experimental study," Heart Rhythm vol. 13, No. 11, Nov. 2016, pp. 2195-2200.

Luiz R. Leite, MD, et al., "Luminal Esophageal Temperature Monitoring with a Deflectable Esophageal Temperature Probe and Intracardiac Echocardiography May Reduce Esophageal Injury during Atrial Fibrillation Ablation Procedures," Circ Arrhythm Electrophysiol, Apr. 2011, pp. 149-156.

José Carlos Pachón Mateos, PhD, "Simplified method for esophagus protection during radiofrequency catheter ablation of atrial fibrillation—prospective study of 704 cases," Braz J Cardiovasc Surg 2015; 30(2), pp. 139-147.

Patrick Müller, MD, et al., "Higher incidence of esophageal lesions after ablation of atrial fibrillation related to the use of esophageal temperature probes," Temperature Probe and Esophageal Lesions After AF Ablation, Heart Rhythm, vol. 12, No. 7, Jul. 2015, pp. 1464-1469.

Dhandrasekar Palaniswamy, MD, et al., "The Extent of Mechanical Esophageal Deviation to Avoid Esophageal Heating during Catheter Ablation of Atrial Fibrillation," JACC: Clinical Electrophysiology, American College of Cardiology Foundation, vol. 3, No. 10, 2017, pp. 1146-1154.

Sheldon M. Singh, MD, et al., "Esophageal Injury and Temperature Monitoring during Atrial Fibrillation Ablation," Circ Arrhythmia Electrophysiol, Aug. 2008, pp. 162-168.

International Search Report and Written Opinion dated Aug. 13, 2019, corresponding to Application No. PCT/US2019/014508.

* cited by examiner

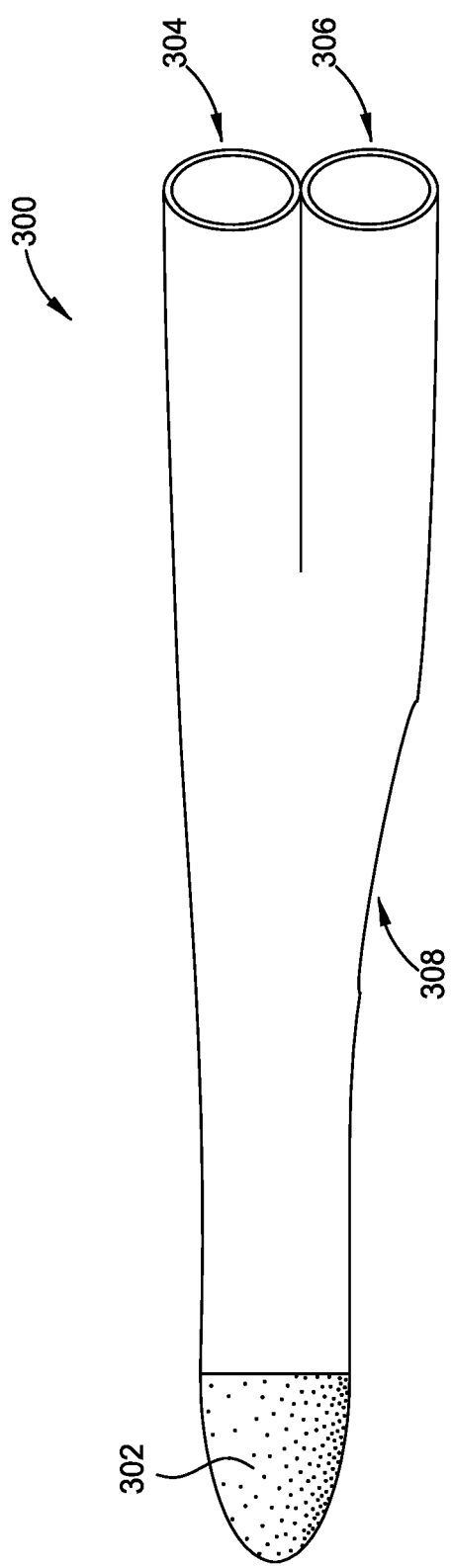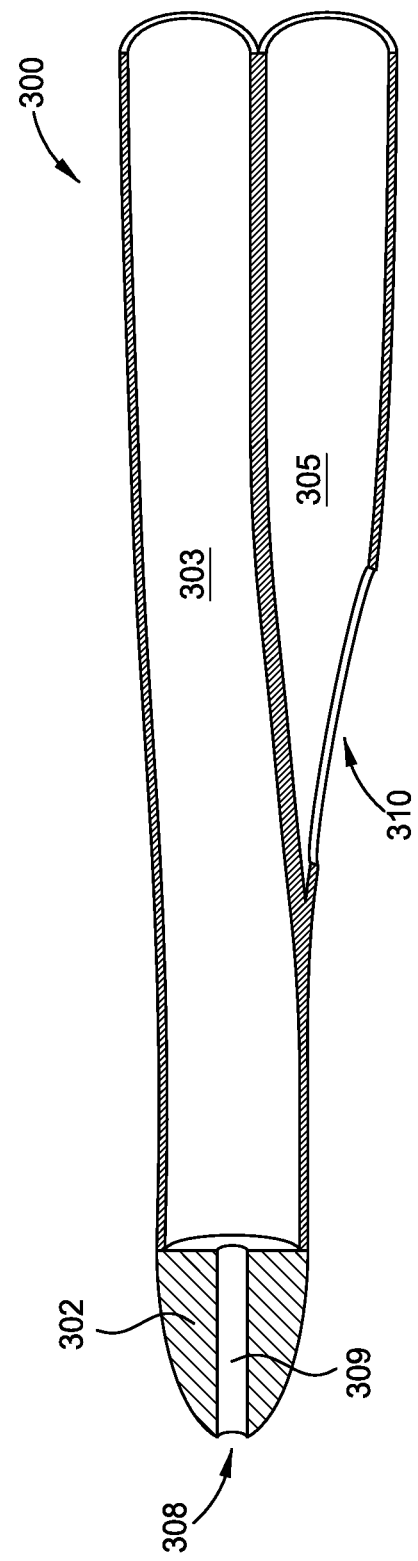
FIG. 3A
FIG. 3B

ESOPHAGEAL MANAGEMENT SYSTEM FOR USE IN DISPLACING AN ESOPHAGUS DURING A MEDICAL PROCEDURE

CLAIM OF PRIORITY UNDER 35 U.S.C. § 119

The present application claims the benefit of priority of U.S. Provisional Patent Application Ser. No. 62/620,001, filed Jan. 22, 2018 and entitled "System and Method for Comprehensive Esophageal Management System that Helps to Manage the Esophagus During Ablation of the Cardiac Chambers and Bronchial Tissue and Effective Monitoring of the Esophageal Temperature using Thermal Measurement Tools, Soft Silicone Outer Tubing and Nitinol Deflectable Deviator," which is hereby incorporated by reference in its entirety.

FIELD OF THE DISCLOSURE

The present disclosure generally relates to medical devices and procedures, and more particularly, to methods and apparatus for managing the esophagus of a subject during a medical procedure.

BACKGROUND

Ablation of cardiac tissue has evolved to be an important therapeutic tool in the management of cardiac arrhythmias, such as atrial fibrillation (AF). Similarly, bronchial tissue ablation has been increasingly used for asthma and other reactive airway disorders. While these ablation therapies have proven to be efficacious, there are serious adverse effects from these therapies due to collateral damage of the surrounding tissues. Injury to the esophagus is a very significant problem in both of these ablation methods due to the relative proximity of the line of ablation to the esophagus.

As illustrated in the example human anatomy of FIG. 1, the left atrium of the heart runs just in front of the esophagus and the trachea, and the bronchi also are in front of the esophagus (i.e., the esophagus is posterior to the bronchi, which is posterior to the left atrium). This proximity makes the esophagus very vulnerable to thermal injury during cardiac or bronchial tissue ablation procedures. One of the most feared complications from thermal injury to the esophagus is atrio-esophageal fistula (AEF) formation. Although the overall incidence of AEF formation is low, AEF is associated with very high morbidity and mortality. Therefore, routine use of such ablation procedures has been limited due to their complexity, resource constraints, and/or concerns about esophageal injury.

A rise in the luminal esophageal temperature (LET) during an ablation procedure has been identified as a surrogate marker for thermal injury to the esophagus. A rise in LET, especially in the anterior wall of the esophagus, may preclude the operator from delivering the desired radio frequency (RF) energy during the ablation procedure. Typically, RF ablation is more tempered on the posterior wall of the left atrium (or bronchi) with significantly lower power, shorter lesion duration, and lower mechanical contact force in an effort to minimize the collateral damage to the esophagus and vagal nerve plexus that are in close proximity to the left atrium (or bronchi). If the esophagus lies exactly posterior to the target site around the pulmonary veins, frequent temperature rises limit the ability to deliver adequate lesion, increase the procedure time, and potentially result in higher pulmonary vein reconnection rates (hence the recurrence rate of AF).

Furthermore, conventional temperature probes for monitoring LET have several problems. For example, conventional temperature probes are typically implemented with thermistors with leads formed by metallic wires for carrying electric current. The thermistor and leads are typically surrounded by an electrically insulative tube or coating, and the distal portion of the probe may include a balloon used to hold the thermistor in place. For measuring LET, inflation of the balloon may separate the thermistor from the tissue, creating an air gap. Other temperature probes without balloons may also have an air gap between the thermistor and the esophageal tissue. This may be due, for example, to the stiffness of the leads, which may move the thermistor out of contact with the tissue. Regardless of the cause for the creation of an air gap, the thermistor may be measuring the temperature of the air within the esophageal lumen or probe balloon, rather than the desired temperature of the tissue, leading to inaccurate measurement. In other words, there may be significant temperature difference depending on whether the thermistor is in contact with the tissue. Moreover, even when this temperature difference is accounted for (e.g., via calibration), this air gap creates a lag between temperature rise of the tissue due to ablation and the temperature rise sensed by the thermistor. Thus, tissue damage may occur before the increase in temperature is sensed. Furthermore, the metal of the thermistor may be itself heated by the ablation procedure, and this "heat sink effect" may cause thermal injury to the nearby tissue.

Improved apparatus and techniques for performing such ablation procedures and LET are desired to avoid tissue damage, while still providing effective treatment.

SUMMARY

Certain aspects of the present disclosure generally relate to apparatus and methods for managing an esophagus of a subject during a medical procedure, such as tissue ablation (e.g., cardiac or bronchial ablation).

Certain aspects of the present disclosure provide a system for managing an esophagus of a subject during a medical procedure. The system generally includes a tube configured for insertion through a mouth and into the esophagus of the subject. The tube generally includes a first port located at a proximal end of the tube and in fluid communication with a distal portion of the tube via a first path, a second port located at the proximal end of the tube, and a third port located between the proximal end of the tube and a distal end of the tube and in fluid communication with the second port via a second path.

Certain aspects of the present disclosure provide a deflector probe for deploying into an esophagus of a subject and capable of displacing the esophagus. The deflector probe generally includes a stylet and a handle coupled to the stylet and disposed at a proximal end of the deflector probe, wherein the handle is configured to control a degree and a direction of deflecting the stylet.

Certain aspects of the present disclosure provide a deflector probe for deploying into an esophagus of a subject and capable of displacing the esophagus. The deflector probe generally includes means for pushing against an inner wall of the esophagus to displace the esophagus, means for rotating the means for pushing, and means for controlling a degree of curvature in the means for pushing.

Certain aspects of the present disclosure provide a temperature probe for deploying into an esophagus of a subject and measuring temperature at one or more locations inside the esophagus. The temperature probe generally includes an optical fiber comprising at least one fiber optic temperature sensor and a radiopacifier disposed at a distal portion of the optical fiber.

Certain aspects of the present disclosure provide a method for monitoring esophageal temperature during a medical procedure. The method generally includes receiving, from at least one optical fiber deployed into an esophagus of a subject, a temperature at each of one or more locations inside the esophagus; determining if the temperature exceeds a threshold; and outputting a control signal to perform an action based on the determination that the temperature exceeds the threshold.

Certain aspects of the present disclosure provide a non-transitory computer-readable medium having instructions stored thereon that, when executed by at least one processor, cause the processor to perform operations for monitoring esophageal temperature during a medical procedure. The operations generally include receiving, from at least one optical fiber deployed into the esophagus of a subject, a temperature at each of one or more locations inside the esophagus; determining if the temperature exceeds a threshold; and outputting a control signal to perform an action based on the determination that the temperature exceeds the threshold.

Certain aspects of the present disclosure provide a method for automatically managing an esophagus of a subject during an ablation procedure. The method generally includes determining a position associated with an ablation catheter used in the ablation procedure; determining a position associated with an esophageal management system inserted into the esophagus and comprising a deflector probe; calculating a distance between the position associated with the ablation catheter and the position associated with the esophageal management system; and based on the distance, controlling adjustment of the deflector probe to adjust a position of the esophagus.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

FIG. 3A is an external view of an example orogastric (OG) tube for use in managing an esophagus during a medical procedure, in accordance with certain aspects of the present disclosure.

FIG. 3B is a cross-sectional view of the OG tube illustrated in FIG. 3A, in accordance with certain aspects of the present disclosure.

DETAILED DESCRIPTION

Certain aspects of the present disclosure provide methods and apparatus for managing an esophagus of a subject during a medical procedure, such as cardiac tissue ablation or bronchial tissue ablation using a catheter. Managing the esophagus may include displacing the esophagus, imaging the esophagus, and/or measuring temperature at one or more locations inside the esophagus.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

As used herein, the term "determining" encompasses a wide variety of actions. For example, "determining" may include calculating, computing, processing, deriving, investigating, looking up (e.g., looking up in a table, a database, or another data structure), ascertaining, and the like. Also, "determining" may include receiving (e.g., receiving information), accessing (e.g., accessing data in a memory), and the like. Also, "determining" may include resolving, selecting, choosing, establishing, and the like.

As used herein, the term "subject" may refer to a human or another animal, such as a pig or a dog.

EXAMPLE MEDICAL SYSTEM

As described above, thermal injury to the esophagus is a very significant problem during cardiac and bronchial tissue ablations due to the relative proximity of the line of ablation to the esophagus. If esophageal injury cannot be prevented with the esophagus in its normal position or an effective ablation treatment cannot be delivered in trying to avoid esophageal injury, then another strategy is to move the esophagus away from the site of ablation. Mechanical deflection of the esophagus away from the ablation site may enable more effective RF lesion delivery, while avoiding esophageal thermal injury.

Figure 1:
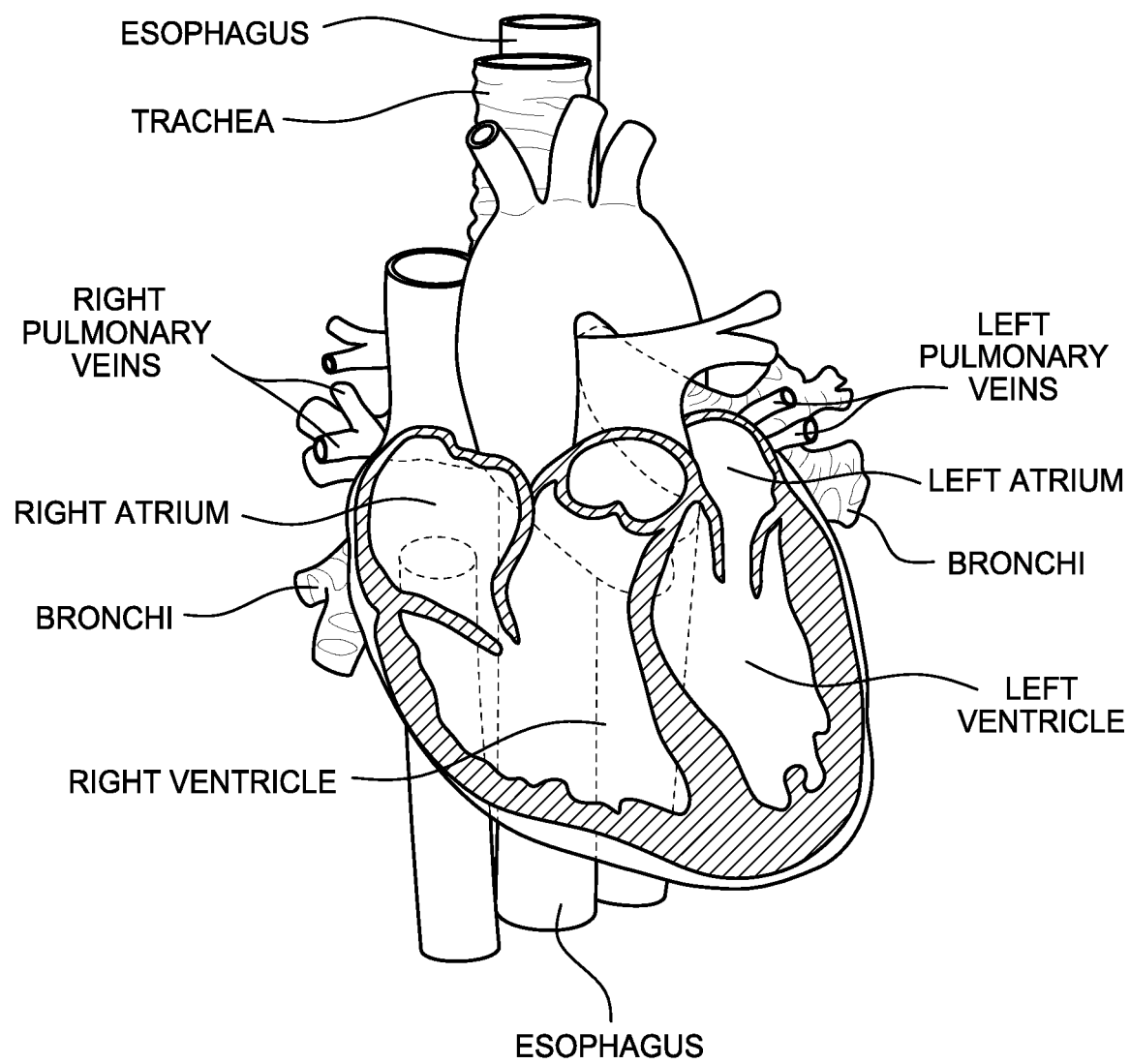
FIG. 1 conceptually illustrates example human anatomy, depicting the relative positions between the heart, the esophagus, the trachea, and the bronchi.
Figure 2:
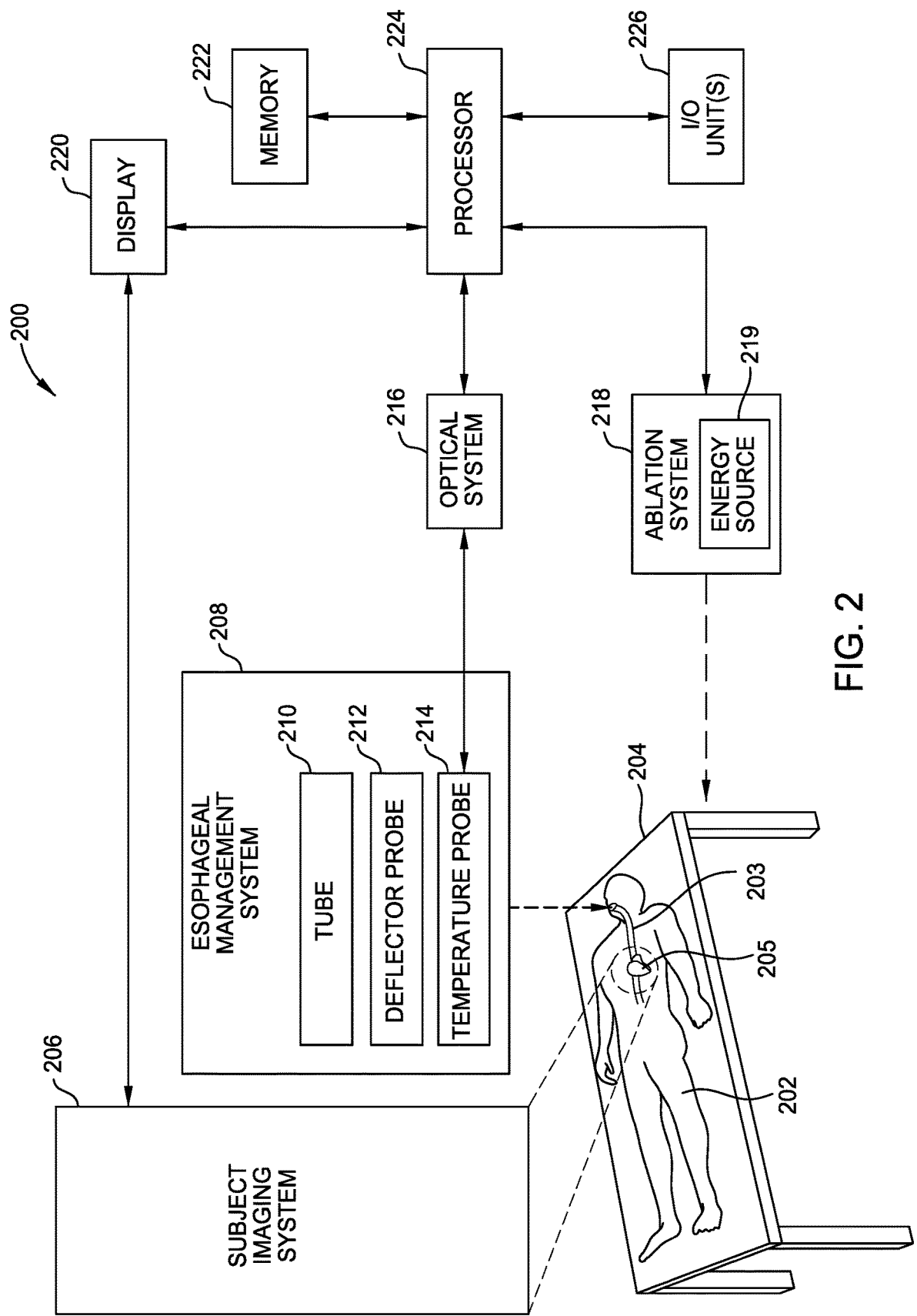
FIG. 2 is a block diagram of an example system for performing an ablation procedure on a subject, including an esophageal management system, in accordance with certain aspects of the present disclosure.

FIG. 2 is a block diagram of an example system 200 for performing an ablation procedure on a subject, in accordance with certain aspects of the present disclosure. The ablation procedure may be performed to treat a heart arrhythmia, such as atrial fibrillation (AF). In the case of arrhythmia treatment, the ablation procedure may involve an epicardial and/or an endocardial ablation, such as a pulmonary vein isolation (PVI) or other ablation of the left atrium. For other aspects, the ablation procedure may be performed to treat a condition of the pulmonary system, such as asthma. In this case, the ablation procedure may entail a bronchial tissue ablation.

For such ablation procedures, it may be desirable to displace the esophagus 203 of a patient away from the heart 205 or bronchi of a subject 202 and/or monitor the temperature of one or more locations within the esophagus during the procedure, in an effort to avoid damage to the esophagus. Therefore, the system 200 may include an esophageal management system 208 with these capabilities. The system 200 may also include a subject imaging system 206, an optical system 216, an ablation system 218, a processor 224, a display 220, memory 222, and one or more input/output (I/O) units 226.

The esophageal management system 208 may include a tube 210. The tube may be an orogastric (OG) tube for inserting into the mouth of the subject 202 while the subject is sedated and intubated on an operating table 204. An example tube is illustrated and described in greater detail below with respect to FIGS. 3A and 3B. Returning to FIG. 2, the esophageal management system 208 may also include a deflector probe 212 and/or a temperature probe 214. The deflector probe 212 may be inserted (e.g., manually or automatically) into a proximal port of the tube 210 and used to displace the esophagus away from the line of ablation. The deflector probe 212 may be designed such that the direction and degree of esophageal displacement may be manually controlled by the operator or automatically controlled by the system (e.g., with a motor to drive the deflector probe). An example deflector probe is illustrated and described in greater detail below with respect to FIGS. 4A-4C. The temperature probe 214 may be inserted into a different proximal port of the same tube 210 and may exit an intermediate port between the proximal end and the distal end of the tube, into the esophagus 203. In this manner, when the esophagus 203 is displaced, the temperature probe 214 may match (e.g., lie adjacent to) the trailing edge of the esophagus. An example temperature probe is illustrated and described in greater detail below with respect to FIG. 5.

Returning to FIG. 2, the subject imaging system 206 may include any of various imaging systems suitable for imaging the internal organs of the subject 202. For example, the subject imaging system 206 may include an X-ray imaging system for performing fluoroscopy. For certain aspects, a contrast medium may be introduced into the esophagus via the tube 210. In such cases, the contrast medium may be selected to be compatible with the subject imaging system 206, or vice versa. In this manner, the subject imaging system 206 may be capable of generating an esophagogram of the subject 204, where an esophagogram is a contrast radiograph of the esophagus. For certain aspects, the subject imaging system 206 may include its own display(s). For other aspects, the subject imaging system 206 may output video signals for display on the display 220, as illustrated in FIG. 2. In some cases, the subject imaging system 206 may be able to determine the location of an ablation catheter, determine the location of the (trailing edge of the) esophagus, and calculate the distance therebetween. At least some of this data may be sent to the processor 224 and/or sent to the display 220 or a display of the subject imaging system 206.

For certain aspects, the temperature probe 214 may be implemented with one or more optical waveguides, such as optical fibers. The optical waveguide may be coupled to one or more sensors for measuring temperature, or the optical waveguide itself may function as an optical sensor. The one or more sensors may include an extrinsic optical sensor (using the optical waveguide to transmit optical signals from a non-optical sensor, such as an electronic sensor coupled to an optical transmitter) and/or an intrinsic optical sensor. An intrinsic optical sensor may use any of various suitable optical techniques for temperature measurement, such as scattering of optical signals (e.g., Raman, Rayleigh, or Brillouin scattering, such as distributed temperature sensing (DTS), based on backscattering of optical signals) or reflection of optical signals (e.g., based on point or continuous fiber Bragg gratings (FBGs)). Each of the optical fibers may comprise a core surrounded by a cladding, where the cladding has a different refractive index than the core to provide for total internal reflection within the optical fiber.

The temperature probe 214 may be coupled to the optical system 216. The optical system 216 may include an optical circulator, a light source for introducing light into the temperature probe 214 via the circulator, and a photodetector for receiving reflected light from the temperature probe via the circulator and converting this reflected light into electrical signals. For certain aspects, the optical system 216 may also include one or more optical splitters for splitting an optical signal for routing in different optical paths. The electrical signals from the optical system 216 may be sent to the processor 224 for processing. In some cases, the optical system 216 may perform signal processing on the electrical signals (e.g., filtering, amplifying, and/or analog-to-digital converting) before transmitting the electrical signals to the processor 224, whereas in other cases, the processor 224 may perform at least some of this signal processing.

The ablation system 218 may comprise any of various suitable configurations using any suitable type of energy source 219 for ablation including, but not limited to, radio frequency (RF), laser, cryo, microwave, low intensity focused ultrasound, high intensity focused ultrasound, and hot water catheter or balloon-based systems.

The processor 224 may interface with the subject imaging system 206, the optical system 216, the ablation system 218, the display 220, the memory 222, and/or the I/O unit(s) 226. For example, the processor 224 may read instructions and/or data from the memory 222 and may write data to the memory. The processor 224 may control the ablation system 218 and may be able to shut down the ablation system in certain aspects, such as where a temperature measured inside the esophagus 203 by the temperature probe 214 exceeds a threshold while performing ablation on the heart 205 or bronchi. In this manner, damage to the esophagus 203 may be avoided. For certain aspects, the processor 224 may be able to control manipulation of the deflector probe 212, such as via one or more motors manipulating a handle mechanism of the deflector probe. For example, in cases where the processor 224 or the subject imaging system 206 determines a distance between the ablation site and the esophagus, the processor 224 can use this distance to automatically manipulate the deflector probe in an effort to adjust this distance.

The processor 224 may receive commands and/or input data from the I/O unit(s) 226. The processor may also send control signals and/or output data to the I/O unit(s) 226. For example, the I/O unit(s) 226 may include a speaker. In this case, if a temperature measured inside the esophagus 203 by the temperature probe 214 (and processed by the optical system 216 and the processor 224) exceeds a threshold while performing ablation on the heart 205 or bronchi, the processor 224 may output a control signal for the speaker to generate an audible alarm. By hearing the audible alarm, the operator performing the medical procedure can halt the ablation procedure and, in some cases, make any desired adjustments (e.g., reposition the esophagus 203 or move the ablation catheter to a different area) before resuming the procedure.

EXAMPLE ESOPHAGEAL MANAGEMENT SYSTEM AND COMPONENTS

As described above, the esophageal management system may include a tube, a deflector probe that may be inserted into a proximal port of the tube, and a temperature probe that may be inserted into another proximal port of the tube. FIG. 3A is an external view of an example orogastric (OG) tube 300 for use in managing an esophagus during a medical procedure, in accordance with certain aspects of the present disclosure. FIG. 3B is a cross-sectional view of the same OG tube 300, in accordance with certain aspects of the present disclosure.

The tube 300 may comprise any of various suitable materials capable of insertion into the esophagus via the mouth and capable of bending as the deflector probe is used to displace the esophagus. The ideal material for the tube 300 will also not cause trauma to the subject. The composition of the tube 300 may also be suitable for receiving and routing a contrast medium into the esophagus. For example, the tube 300 may be composed of silicone or polyvinyl. For certain aspects, the outer surface of the tube 300 may be coated, for example, with a lubricant to aid insertion into the esophagus (e.g., down to the lower end of the esophagus below the heart). For certain aspects, one or more inner surfaces of the tube 300 may be coated (e.g., with a lubricant) to enable easy insertion of the deflector probe and/or the temperature probe. For example, the tube 300 may be manufactured and sold with prelubricated inner surfaces.

The tube 300 may be graded as shown, wherein the outer diameter of the tube increases from a distal end to the proximal end. As a non-limiting example, the tip may have an outer diameter in a range of 6 to 10 Fr (e.g., 8 Fr), whereas the proximal end may have an outer diameter in a range of 12 to 16 Fr (e.g., 14 Fr).

The tube 300 may have two lumens 303, 305 providing two paths within the tube. For certain aspects, the first lumen 303 (e.g., a first path) may be isolated from the second lumen 305. The first lumen 303 (e.g., a second path) may be accessed via a first port 304, whereas the second lumen 305 may be accessed via a second port 306. The first lumen 303 and the first port 304 are configured for insertion of the deflector probe into the tube 300. For certain aspects, a contrast medium may be introduced into the tube 300 via the first port 304. The second lumen 305 and the second port 306 are configured for insertion of the temperature probe into the tube 300. For certain aspects, a contrast medium may be introduced into the tube 300 via the second port 306, in addition or as an alternative to the first port 304. The contrast medium allows an operator to visualize the course and extent of the esophagus.

The tube 300 may also have a third port 310, which is an intermediate port located between the proximal and distal ends of the tube and may act as an exit port for the second lumen 305. Thus, when a temperature probe and/or a contrast medium is introduced into the second lumen 305 via the second port 306, the temperature probe and/or the contrast medium may exit the second lumen 305 via the third port 310. For example, the third port 310 may be located approximately 20 cm from the distal tip of the tube 300, which may allow for proper exposure and assessment of the esophagus behind the left atrium by the temperature probe.

For certain aspects, the tube 300 may include a fourth port 308 at a distal portion of the tube. For example, the fourth port 308 may be located at the distal end (e.g., the tip) of the tube 300, as shown in FIG. 3B. The fourth port 308 may be in fluid communication with the first port 304 via the first lumen 303. In this manner, contrast medium, lubrication, or another fluid injected into the first lumen 303 may exit the tube 300 via the fourth port 308.

For certain aspects, the tube 300 may include a radiopacifier 302 at a distal portion of the tube (e.g., at the tip, as depicted in FIGS. 3). The radiopacifier 302 is radiopaque, inhibiting penetration by radio frequency and X-ray signals. Therefore, the radiopacifier 302 will be clearly visible in X-ray images (e.g., fluoroscopy), providing for easy insertion of the distal end of the tube 300 to the desired location within the esophagus (e.g., below the heart).

The diameter of the fourth port 308 (and/or the channel 309 through the radiopacifier 302) may be designed to be smaller than a distal end of the deflector probe, such that the deflector probe will not be able to penetrate the end of the tube 300. In this manner, the distal portion of the deflector probe inserted into the tube 300 will remain confined within the tube and unexposed, thereby providing protection to the esophagus.

The single tube 300 with two lumens 303, 305 is an improvement over other designs, where two or more separate tubes may be used (e.g., one tube for a deflector probe and another tube for a temperature probe). A single tube is easier and faster for an operator to deploy than two separate tubes. Furthermore, a single tube reduces discomfort to the subject and decreases the risk of complications arising from tube insertion.

Figure 4A:
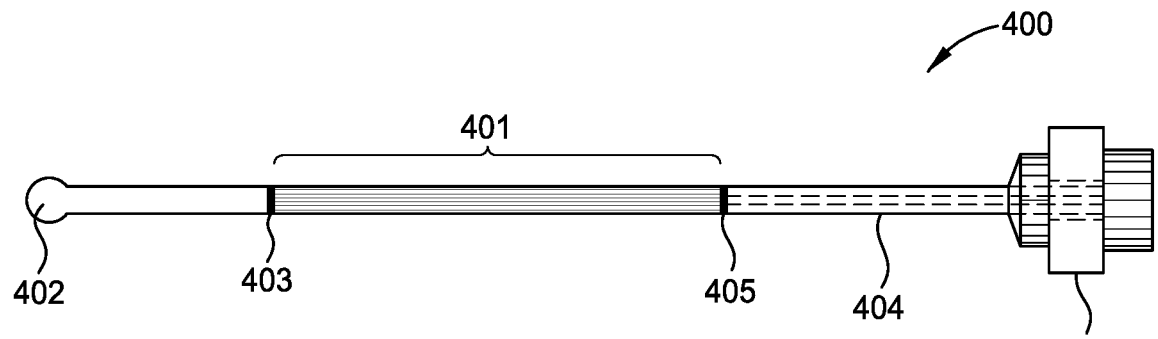
FIG. 4A illustrates an example deflector probe for displacing the esophagus, configured in a neutral position, in accordance with certain aspects of the present disclosure.

FIG. 4A illustrates an example deflector probe 400 for displacing the esophagus, in accordance with certain aspects of the present disclosure. The deflector probe 400 may be used, for example, as the deflector probe 212 in the esophageal management system 208 of FIG. 2. The deflector probe 400 may include a handle 406, a shaft 404, and a stylet 401. The deflector probe 400 is depicted in FIG. 4 in the neutral position, where the stylet 401 has no deviation (e.g., no curve). The neutral position of the deflector probe 400 may be used for insertion of the deflector probe into the tube 300.

Disposed at a proximal end of the deflector probe 400, the handle 406 may comprise a rotatable knob and/or a push-pull mechanism, for example. For certain aspects implemented with a knob, the knob may have a textured surface or grooves to provide grip and tactile sensation for the operator during esophageal deflection using the deflector probe 400. For other aspects, the deflector probe 400 may be designed to be mechanically manipulated by a motor and/or a robot, for example, rather than by a human operator. The handle 406 may be coupled to the shaft 404, which may be hollow. In the case of a knob, the knob may be configured to rotate with respect to the shaft 404. The handle 406 and/or the shaft 404 may be composed of plastic or any other suitable material.

The stylet 401 may be coupled to (e.g., mechanically jointed with) the handle 406, and at least a portion of the stylet may traverse the shaft 404. The stylet 401 may be implemented as one or more wires, which may comprise nitinol or any other suitable material. For certain aspects, the stylet 401 may comprise a polyvinyl tubing with the wire(s) disposed therein. In this case, the tubing of the stylet 401 may be coupled to the shaft 404, whereas the wire(s) may traverse the shaft for coupling to the handle 406. Since the shaft 404 may be straight, the wire(s) of the stylet 401 may be prevented from curving within the shaft.

Figure 4B:
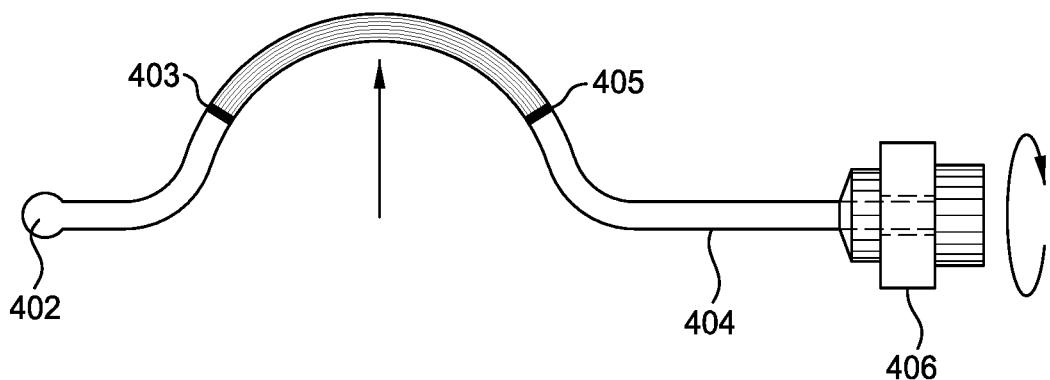
FIG. 4B illustrates the deflector probe of FIG. 4A, configured to deviate the esophagus in a first direction, in accordance with certain aspects of the present disclosure.

The one or more wires within the stylet 401 may be controlled by rotational elements to rotate the wire(s), push-pull elements to adjust the curvature of the wire(s), or a combination thereof. For certain aspects, the natural body-temperature-driven influence on the stiffness of the material in the wire(s) (e.g., nitinol) may be employed to enhance the deviation capability of the deflector probe 400. From the neutral position, translation of the handle 406 (e.g., pushing or pulling axially with respect to the longitudinal axis of the shaft 404) may be used to create a curve in the stylet 401 and control the degree of curvature. Rotation of the handle 406 in a clockwise direction causes the stylet 401 to deflect in a first direction, as illustrated in FIG. 4B. Rotation of the handle 406 in a counterclockwise direction causes the stylet 401 to deflect in a second direction opposite from the first direction, as portrayed in FIG. 4C. In this manner, the stylet 401 can be used to push one edge of the esophagus (i.e., the leading edge) away from the designated ablation site, such that there is sufficient distance between the other edge of the esophagus (i.e., the trailing edge) and the ablation site to minimize, or at least reduce, thermal injury to the esophagus. The rotation of the deflector probe enables the operator to move the esophagus to the left or right, away from the site of ablation.

Figure 4C:
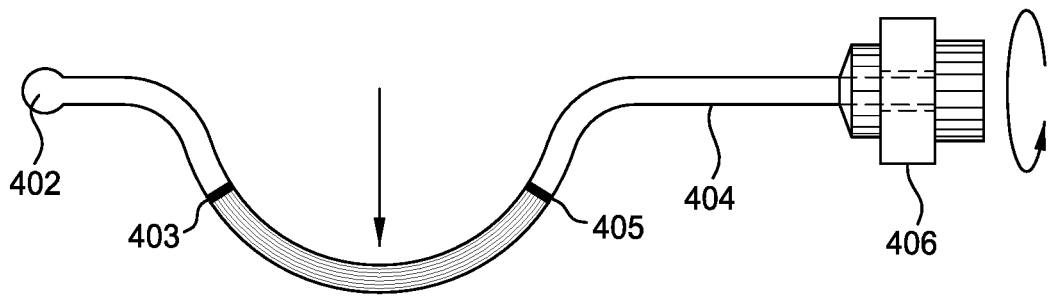
FIG. 4C illustrates the deflector probe of FIG. 4A, configured to deviate the esophagus in a second direction, opposite the first direction of FIG. 4B, in accordance with certain aspects of the present disclosure.

For certain aspects, the deflector probe 400 may also include one or more radiopaque markers 403, 405. For certain aspects, the radiopaque markers 403, 405 may be disposed along a length of the stylet 401, such as near opposite ends of the stylet, as illustrated in FIGS. 4A-4C. The distance between the radiopaque markers 403, 405 may be selected such that the distal radiopaque marker 403 is disposed below the heart at a lower end of the esophagus and the proximal radiopaque marker 405 is disposed above the heart at an upper end of the esophagus when the deflector probe 400 is inserted into a tube 300 deployed in the esophagus.

For certain aspects, the tip 402 of the deflector probe 400 may be ball-shaped (i.e., spherical) as illustrated in FIG. 4A. For other aspects, the tip 402 may assume any other suitable shape that is smooth and curved to prevent damage to the tube 300 during insertion of the deflector probe 400 into the tube and/or extraction from the tube. Other suitable shapes may include, but are not limited to, oval, barrel, or teardrop shapes.

Figure 5:
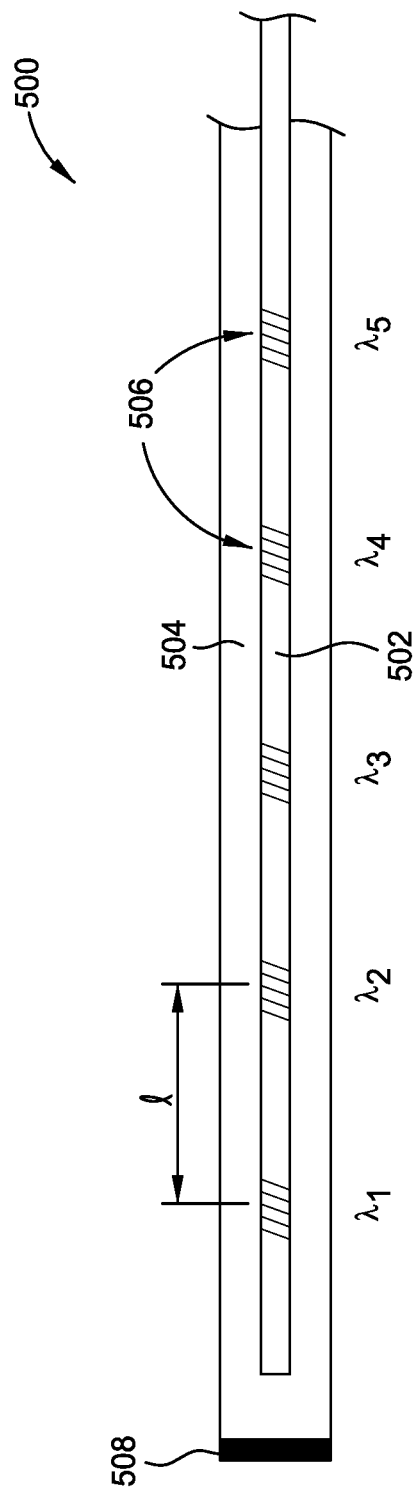
FIG. 5 illustrates an example temperature probe for measuring temperature within the esophagus, in accordance with certain aspects of the present disclosure.

FIG. 5 illustrates an example temperature probe 500 for measuring temperature at one or more locations within the esophagus, in accordance with certain aspects of the present disclosure. The temperature probe 500 may be used, for example, as the temperature probe 214 in the esophageal management system 208 of FIG. 2. The temperature probe 500 may be implemented with one or more optical waveguides, such as optical fibers. Each of the optical fibers may comprise a core 502 surrounded by a cladding 504, where the cladding has a different refractive index than the core 502 to provide for total internal reflection within the optical fiber.

In the example of FIG. 5, the temperature probe 500 includes a single optical fiber with multiple fiber Bragg gratings (FBGs) 506. For certain aspects, the FBGs 506 may be written into the core 502 of the optical fiber, while in other aspects, optical waveguides comprising the FBGs 506 may be spliced together. Each of the FBGs 506 may have a different characteristic wavelength ($\lambda_o$), the center of the narrow wavelength band at which the particular FBG reflects wavelengths in the optical spectrum. The characteristic wavelength of an FBG 506 is sensitive to temperature, and therefore, changes in a nominal characteristic wavelength reflected by a particular FBG may be used to measure temperature shifts. By using FBGs 506 with different characteristic wavelengths, wavelength division multiplexing (WDM) may be utilized (e.g., by the optical system 216) to distinguish between light reflections from the different FBGs, and hence, temperature measured at different areas along the optical fiber.

In the example of FIG. 5, the temperature probe includes five FBGs 506 having characteristic wavelengths $\lambda_1$, $\lambda_2$, $\lambda_3$, $\lambda_4$, and $\lambda_5$, spaced along a length of the optical fiber (e.g., a distal portion of the fiber). For example, the length (l) along the optical fiber between an adjacent pair of FBGs 506 may be in a range from 0.5 to 1.5 cm, such as l=1.0 cm. Although five FBGs 506 are shown, the number of FBGs in the temperature probe 500 may be any suitable number, such as between 1 and 10, or more typically between 4 and 8. The number of FBGs 506 and the length between any adjacent pair of FBGs 506 may be selected to provide adequate temperature-measurement coverage of the relevant length of the esophagus (e.g., the entire length of the esophagus behind the left atrium of the heart) with the desired spatial resolution.

For other aspects, the temperature probe may include multiple optical fibers, each comprising one or more FBGs. In this case, the multiple optical fibers may be bundled in the temperature probe, such that the multiple fibers may be inserted together, rather than individually inserted. This allows for easier and faster placement within the tube of the esophageal management system. Other aspects of the example temperature probe 500 of FIG. 5 may be included and/or function similarly in such a temperature probe with multiple optical fibers.

For certain aspects, the temperature probe 500 may include a radiopacifier 508, as illustrated in FIG. 5. The radiopacifier 508 may be disposed at a distal portion of the temperature probe 500, such as at the distal end of the optical fiber. The radiopacifier 508 is radiopaque, thereby allowing the temperature probe 500 to be clearly visible during fluoroscopy and, thus, easily positioned (and repositioned) at the desired location within the esophagus.

The use of optical waveguides provides several advantages over the metal thermistors of conventional temperature probes. First, the FBGs have a truly linear correlation between wavelength and temperature, unlike thermistors. In addition, the FBGs are typically made of glass (e.g., silica) or plastic, rather than metal. Consequently, the heat sink effect of the metal thermistors during ablation and the tissue damage caused therefrom is altogether avoided by FBGs, and the FBGs create no metal artifacts during dynamic MRI or CT imaging. As another advantage, the FBGs do not exhibit temperature overestimation due to direct light absorption during laser procedures, the sonification effect during low intensity continuous ultrasound (LICU) or high intensity focused ultrasound (HIFU), or due to high heat conductivity of metallic wires during cryo ablation. Furthermore, the non-metallic FBGs do not exhibit temperature underestimation for microwave, RF, or hot water ablation, in contrast with thermistors.

For certain aspects, one or more of the FBGs may be a linearly chirped fiber Bragg grating (LCFBG). With an LCFBG, the temperature probe can achieve a spatial resolution of 75 μm on a 1.5 cm length of fiber, providing a far more accurate temperature measurement than can be accomplished with conventional thermistor temperature probes. For example, a multipoint LCFBG probe with 5 mm gratings at 10 mm intervals may be used to cover a desired esophageal length to accurately assess esophageal temperature and degree of tissue contact.

For other aspects, the temperature probe may be implemented with at least one optical fiber, where the optical fiber is itself the optical temperature sensor. Such temperature probes may be based on distributed temperature sensing (DTS), utilizing backscattered reflections of optical signals introduced into the optical fiber, the backscattered reflections being along a length of the core of the optical fiber.

Figure 6:
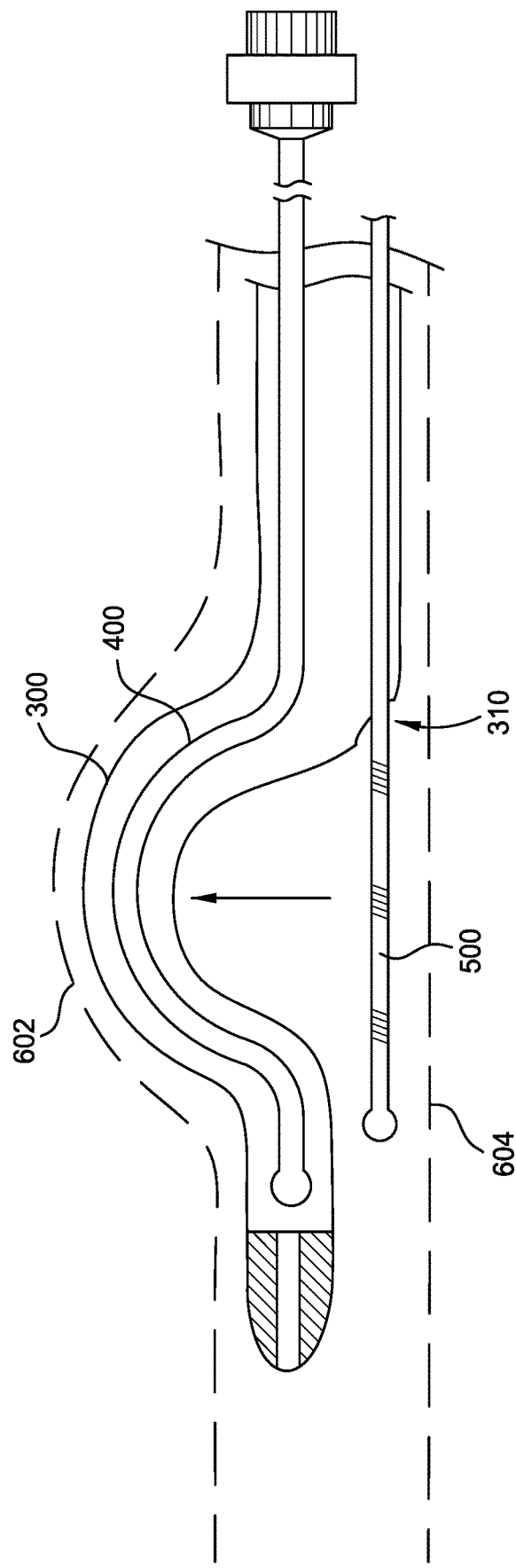
FIG. 6 is a cross-sectional view conceptually illustrating the esophageal management system in use, in accordance with certain aspects of the present disclosure.

FIG. 6 is a cross-sectional view conceptually illustrating an esophageal management system 600 in use, in accordance with certain aspects of the present disclosure. The esophageal management system 600 may be used, for example, as the esophageal management system 208 of FIG. 2. The esophageal management system 600 may include a tube 300, a deflector probe 400 inserted into the first lumen 303 of the tube 300 via the first port 304, and a temperature probe 500 inserted into the second lumen 305 of the tube 300 via the second port 306. The temperature probe 500 may also exit the second lumen 305 via a third port 310.

As described above, manipulating (e.g., turning and/or translating) the handle 406 of the deflector probe 400 causes the stylet 401 to curve in a desired direction. As the stylet 401 curves, the stylet pushes the tube 300 against the inner wall of the esophagus and causes displacement of the esophagus in a particular direction. The outer wall of the esophagus at the forefront of this deviation is referred to as the leading edge 602 of the esophagus, whereas the outer wall of the esophagus at the back end of this deviation is referred to as the trailing edge 604 of the esophagus. The objective of the esophageal displacement is to move the trailing edge 604 of the esophagus a suitable distance away from the ablation site. Therefore, the handle 406 may be manipulated until a desired degree and direction of esophageal displacement is achieved (e.g., the trailing edge 604 is far enough away from the planned line of ablation).

Since the temperature probe 500 exits the second lumen 305 via the third port 310, the temperature probe 500 may match the trailing edge 604 of the esophagus. In other words, the temperature probe 500 may be inserted into the esophagus and initially positioned, but may be forced against the inner wall of the esophagus as the trailing edge 604 is pulled by the pushing of the stylet 401 on the opposite inner wall. In this manner, the temperature probe 500 may lie adjacent to the inner wall of the esophagus closest to the trailing edge 604 during esophageal displacement. Therefore, the temperature probe 500 may be in the most suitable position for accurate temperature measurement at one or more locations along the trailing edge 604 of the esophagus. Although the temperature probe 500 and the trailing edge 604 are depicted as being straight in FIG. 6 to conceptually illustrate the curving of the stylet 401 away from the temperature probe and to exaggerate the slight stretching of the esophagus during displacement, the reader will understand that the displaced esophagus will likely have a curved trailing edge 604 and that the temperature probe 500 will match the trailing edge.

EXAMPLE OPERATIONS FOR USING AN ESOPHAGEAL MANAGEMENT SYSTEM

Figure 7:
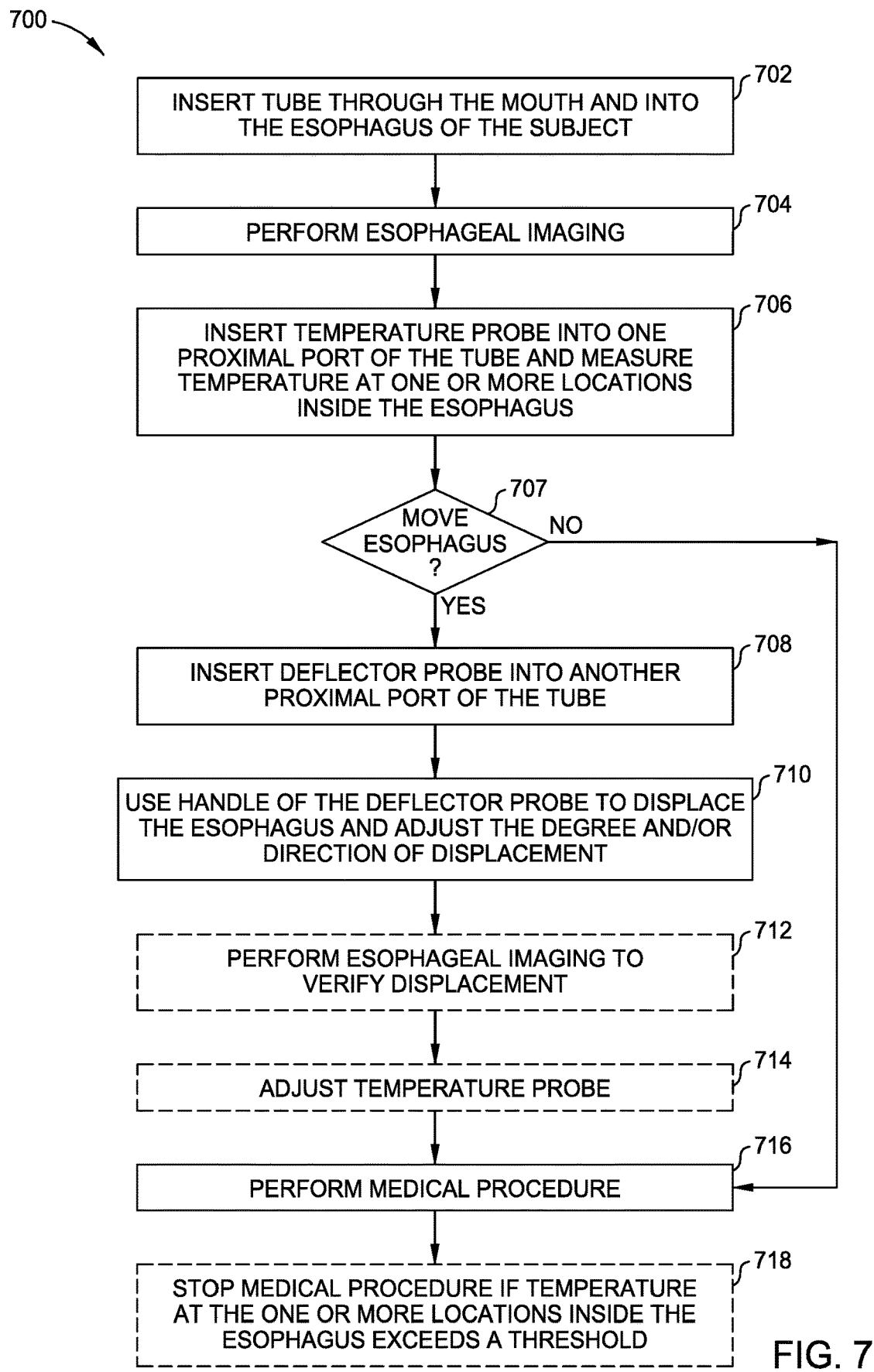
FIG. 7 is a flow diagram of example operations for using the esophageal management system, in accordance with certain aspects of the present disclosure.

FIG. 7 is a flow diagram of example operations 700 for using an esophageal management system (e.g., an esophageal management system 208 or 600), in accordance with certain aspects of the present disclosure. At least some of the operations 700 may be performed by a medical system, such as the system 200 of FIG. 2, while other operations 700 may be performed by at least one operator (e.g., a physician, a veterinarian, and/or other medical staff).

The operations 700 may begin, at block 702, after the subject (e.g., subject 202) is sedated and intubated. At block 702, the operator may insert a tube (e.g., tube 210 or 300) through the mouth and into the esophagus of the subject, for example, to traverse the gastroesophageal (GE junction). At block 704, the system performs imaging (e.g., fluoroscopy) of the esophagus. For example, an esophagogram may be performed using 20 to 30 cc of a contrast medium to visualize the position of the esophagus in relation to the posterior wall of the left atrium. This may also help the operator to understand the breadth of the esophagus and determine if there are any esophageal anomalies before inserting a deflector probe. For certain aspects, the contrast medium may be introduced into a proximal port (e.g., the first port 304) of the tube and may exit via a distal port (e.g., the fourth port 308) in the tube (e.g., at the tip of the tube) or via an intermediate port (between the proximal end and the distal end) (e.g., the third port 310).

At block 706, the operator inserts a temperature probe (e.g., temperature probe 214 or 500) into a proximal port (e.g., the second port 306) of the tube. Using the temperature probe, the system measures the temperature at one or more locations inside the esophagus. For example, the temperature probe may be inserted to line up with the tube in the esophagus to measure the esophageal temperature during ablation of the posterior wall of the left atrium. The specially designed orogastric (OG) tube allows for the placement of the temperature probe therethrough and helps align the temperature probe with the trailing edge of the esophagus, instead of being pulled away, as may occur with conventional designs. Aligning the temperature probe with the trailing edge utilizing the specially designed tube significantly improves the sensitivity of temperature measurement from the line of ablation. The specially designed tube also removes the need for separate esophageal manipulation (conventionally, the temperature probe and the OG tube are inserted separately into the esophagus). For certain aspects, the system may display the temperature measured by a selected set of the one or more locations. The system may use a color-coded scale for the set of temperature(s) displayed on a monitor (e.g., display 220).

At block 707, the operator (or the system, in some cases) determines whether to move the esophagus. For example, the operator (or the system) may determine based on the esophagogram if the esophagus is currently positioned in the line of ablation or within a certain distance of the ablation. If not, the operations 700 may proceed to block 716 as described below. If the operator (or the system) decides to move the esophagus at block 707, then at block 708, the operator (or the system, in some cases) inserts a deflector probe (e.g., deflector probe 212 or 400) into a proximal port (e.g., the first port 304) of the tube, different from the proximal port used for the temperature probe. For certain aspects, the deflector probe may include two radiopaque markers (e.g., markers 403 and 405, also referred to as radiopacifiers), such that the deflector probe may be inserted until the radiopaque markers are located at upper and lower ends of the esophagus (e.g., above the top of the heart and below the bottom of the heart). In this manner, the markers help the operator (or the system) locate the deflector probe in the desired position.

At block 710, the operator may utilize a handle (e.g., the handle 406) at the proximal end of the deflector probe to manually displace the esophagus. For other aspects, the system may manipulate the handle of the deflector probe. For example, the handle may be motor-driven automatically (e.g., under control of the processor 224). In either case, the handle may be manipulated (e.g., translated and/or rotated) to adjust the degree and/or direction of the esophageal displacement. For certain aspects, a stylet (e.g., stylet 401) of the deflector probe may be curved in the desired direction and with the desired amount to move the esophagus as the stylet curves. This deviation may be used, for example, to move the esophagus away from the line of ablation.

At optional block 712, the system may perform esophageal imaging again in an effort to verify displacement of the esophagus. Such imaging may identify the trailing edge (e.g., edge 604) of the esophagus and the distance of the trailing edge from the line of ablation, for example. At optional block 714, the operator may adjust the temperature probe based on the esophageal imaging performed at block 712. For example, the temperature probe may be repositioned to match (e.g., lie against) the trailing edge of the esophagus for a more accurate assessment of the esophageal temperature rise during ablation.

At block 716, the operator and/or the system performs the medical procedure (e.g., catheter ablation, such as PVI). If the temperature at the one or more locations inside the esophagus exceeds a threshold, then at optional block 718, the medical procedure may be stopped (e.g., manually by the operator or automatically by the system, such as by powering off an ablation energy source, such as source 219). In this manner, damage to the esophagus may be avoided.

EXAMPLE OPERATIONS FOR MONITORING ESOPHAGEAL TEMPERATURE

Figure 8:
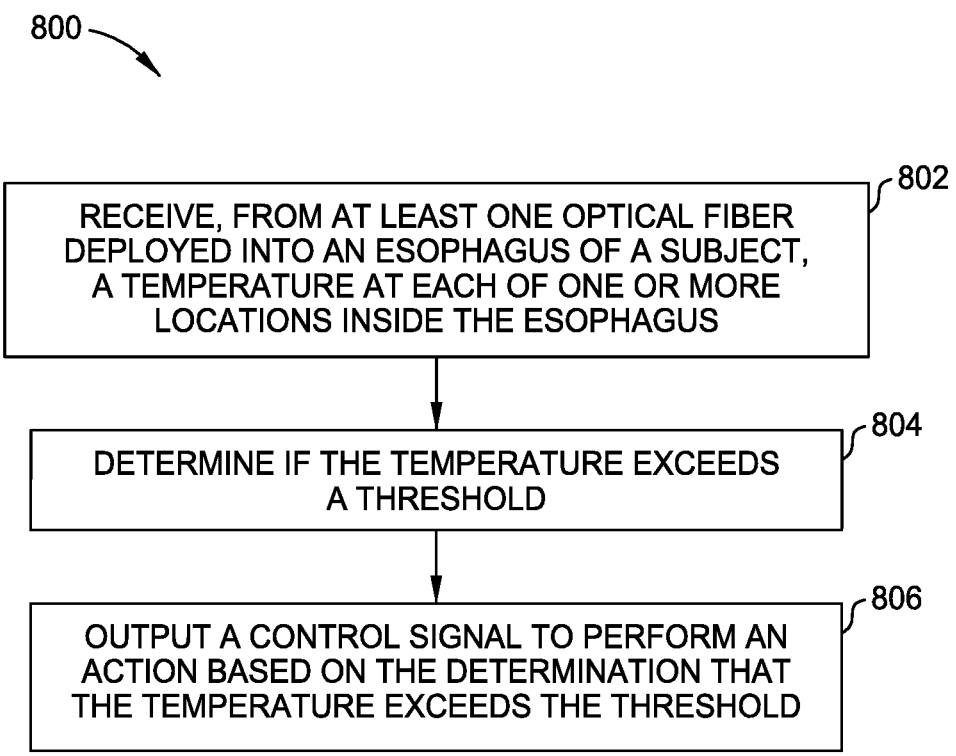
FIG. 8 is a flow diagram of example operations for monitoring esophageal temperature during a medical procedure, in accordance with certain aspects of the present disclosure.

FIG. 8 is a flow diagram of example operations 800 for monitoring esophageal temperature during a medical procedure performed on a subject (e.g., a human patient or another animal), in accordance with certain aspects of the present disclosure. The operations 800 may be performed by at least one processor, such as the processor 224 of FIG. 2.

The operations 800 may begin, at block 802, with the processor receiving a temperature at each of one or more locations inside the esophagus of the subject. The temperature at each location may be received from at least one optical fiber deployed into the esophagus. At block 804, the processor determines if the temperature exceeds a threshold. At block 806, the processor outputs a control signal to perform an action based on the determination that the temperature exceeds the threshold at block 804.

According to certain aspects, the operations 800 may further involve outputting one or more video signals for displaying the temperature at a selected set of the one or more locations inside the esophagus. The video signals may be intended for one or more display units, such as display 220 in FIG. 2. For certain aspects, the one or more video signals encode one or more color-coded versions of the temperature at the selected set of the one or more locations inside the esophagus.

According to certain aspects, the medical procedure includes an ablation procedure. In this case, the control signal may be configured to shut down an ablation energy source (e.g., ablation energy source 219 in FIG. 2). The ablation energy source may, for example, be a radio frequency (RF) power amplifier and/or frequency synthesizer in an ablation system, such as the ablation system 218 of FIG. 2.

According to certain aspects, the optical fiber comprises a plurality of fiber Bragg gratings (FBGs) having different characteristic wavelengths.

According to certain aspects, the control signal is configured to control a speaker to sound an audible alarm based on the determination at block 804 that the temperature exceeds the threshold.

According to certain aspects, at least one of the locations is along a trailing edge of the esophagus due to deviation of the esophagus from a normal esophageal position by a deflector probe (e.g., deflector probe 212 in FIG. 2).

Certain aspects of the present disclosure provide a system for managing an esophagus of a subject during a medical procedure. The system generally includes a tube configured for insertion through a mouth and into the esophagus of the subject. The tube generally includes a first port located at a proximal end of the tube and in fluid communication with a distal portion of the tube via a first path, a second port located at the proximal end of the tube, and a third port located between the proximal end of the tube and a distal end of the tube and in fluid communication with the second port via a second path.

Certain aspects of the present disclosure provide a deflector probe for deploying into an esophagus of a subject and capable of displacing the esophagus. The deflector probe generally includes a stylet and a handle coupled to the stylet and disposed at a proximal end of the deflector probe, wherein the handle is configured to control a direction and a degree of deflecting the stylet.

According to certain aspects, the handle is configured such that, a clockwise rotation of the handle causes the stylet to deflect in a first direction and a counterclockwise rotation of the handle causes the stylet to deflect in a second direction opposite from the first direction.

According to certain aspects, the deflector probe further includes one or more radiopaque markers disposed along a length of the stylet.

According to certain aspects, the stylet comprises a nitinol wire.

According to certain aspects, the handle is configured such that an axial translation of the handle controls a degree of curvature in the stylet.

According to certain aspects, the deflector probe further includes a shaft coupled to the handle and having a bore (i.e., the shaft is hollow). The stylet may traverse the bore of the shaft.

Certain aspects of the present disclosure provide a deflector probe for deploying into an esophagus of a subject and capable of displacing the esophagus. The deflector probe generally includes means for pushing against an inner wall of the esophagus to displace the esophagus, means for rotating the means for pushing, and means for controlling a degree of curvature in the means for pushing. For example, the means for pushing may include a stylet (e.g., stylet 401), which may be composed of one or more wires. The means for rotating may include a rotational element coupled to the means for pushing. For example, the means for rotating may be implemented as a rotatable knob. The means for controlling the degree of curvature may be implemented with a push-pull mechanism, for example.

According to certain aspects, at least one of the means for rotating or the means for controlling are disposed at a proximal end of the deflector probe.

According to certain aspects, the deflector probe further includes means for visualizing the means for pushing during medical imaging. For example, the means for visualizing may include one or more radiopacifiers for use during fluoroscopy.

Certain aspects of the present disclosure provide a temperature probe for deploying into an esophagus of a subject and measuring temperature at one or more locations inside the esophagus. The temperature probe generally includes an optical fiber comprising at least one fiber optic sensor and a radiopacifier disposed at a distal portion of the optical fiber.

According to certain aspects, the optical fiber comprises a core and a cladding surrounding the core. In this case, the at least one fiber optic temperature sensor may include one or more fiber Bragg gratings (FBGs) disposed in the core of the optical fiber. For certain aspects, the one or more FBGs comprise a plurality of FBGs spaced along a length of the optical fiber. For certain aspects, each of the plurality of FBGs comprises a different characteristic wavelength. For certain aspects, a distance between an adjacent pair of the plurality of FBGs is in a range from 0.5 to 1.5 cm.

According to certain aspects, the optical fiber comprises a core and a cladding surrounding the core. In this case, the at least one fiber optic temperature sensor may comprise a distributed temperature sensor configured to utilize backscattered reflections of light along a length of the core.

According to certain aspects, the radiopacifier is disposed at a distal tip of the optical fiber.

Certain aspects of the present disclosure provide a method for automatically managing an esophagus of a subject during an ablation procedure. The method generally includes determining a position associated with an ablation catheter used in the ablation procedure; determining a position associated with an esophageal management system inserted into the esophagus and comprising a deflector probe; calculating a distance between the position associated with the ablation catheter and the position associated with the esophageal management system; and based on the distance, controlling adjustment of the deflector probe to adjust a position of the esophagus.

Any of the operations described above, such as the operations 700 or 800, may be included as instructions in a computer-readable medium for execution by a processing system. The (non-transitory) computer-readable medium may comprise any suitable memory or other storage device for storing instructions, such as read-only memory (ROM), random access memory (RAM), flash memory (e.g., USB flash drive), an electrically erasable programmable ROM (EEPROM), a compact disc ROM (CD-ROM), a floppy disk, or a digital versatile disc ROM (DVD-ROM).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein (including the claims that follow), a phrase referring to "at least one of" a list of items refers to any combination of those items, including single members. As an example, "at least one of: x, y, and z" is intended to cover: x, y, z, x-y, x-z, y-z, x-y-z, and any combination thereof (e.g., x-y-y and x-x-y-z).

While the foregoing is directed to certain aspects of the present disclosure, other and further aspects may be devised without departing from the basic scope thereof, and the scope thereof is determined by the claims that follow.

What is claimed is:

1. A method for monitoring esophageal temperature during a medical procedure, the method comprising:
    advancing at least one optical fiber into an esophagus of a subject, wherein the at least one optical fiber comprises one or more sensors configured to measure temperature;
    advancing a probe to deflect at least a portion of the esophagus from a first location to a second location;
    measuring temperature with the one or more sensors of the at least one optical fiber from at least the second location;
    determining if the temperature exceeds a threshold; and
    outputting a control signal to perform an action based on the determination that the temperature exceeds the threshold.

2. The method of claim 1, further comprising outputting one or more video signals for displaying the temperature measured from at least the second location inside the esophagus.

3. The method of claim 2, wherein the one or more video signals encode one or more color-coded versions of the temperature measured from at least the second location inside the esophagus.

4. The method of claim 1, wherein the medical procedure comprises an ablation procedure and wherein the control signal is configured to shut down an ablation energy source.

5. The method of claim 1, wherein the at least one optical fiber comprises a plurality of sensors, and wherein the plurality of sensors comprises a plurality of fiber Bragg gratings (FBGs) having different characteristic wavelengths.

6. The method of claim 5, wherein the plurality of FBGs are spaced along a length of the at least one optical fiber and a distance between an adjacent pair of the plurality of FBGs is in a range from 0.5 to 1.5 cm.

7. The method of claim 1, wherein the control signal is configured to control a speaker to sound an audible alarm based on the determination that the temperature exceeds the threshold.

8. The method of claim 1, further comprising:
    in response to the temperature measured from at least the second location inside the esophagus exceeding the threshold, triggering a power off of an ablation energy source.

9. The method of claim 1, wherein a radiopacifier is disposed at a distal portion of the at least one optical fiber.

10. The method of claim 1, wherein the at least one optical fiber includes a plurality of optical fibers.

11. The method of claim 10, wherein each optical fiber of the plurality of optical fibers comprise a corresponding plurality of fiber Bragg gratings (FBGs) having different characteristic wavelengths.

12. The method of claim 1, further comprising:
controlling at least one of a direction, a displacement, and an orientation of the probe based at least in part on the temperature of the second location inside the esophagus.

13. The method of claim 1, wherein the medical procedure comprises an ablation procedure, the method further comprising:
determining a location of an ablation catheter to perform the medical procedure.

14. The method of claim 1, wherein the medical procedure comprises an ablation procedure, the method further comprising:
determining a distance between at least the second location and an ablation site;
determining whether the distance is greater than a minimum threshold distance;
in response to determining that the distance is lower than the minimum threshold distance, controlling the probe to deflect the portion of the esophagus from the second location to a third location.

* * * * *